United States Patent
Lee et al.

(10) Patent No.: US 8,525,126 B2
(45) Date of Patent: Sep. 3, 2013

(54) UV FLUID STERILIZER SUITABLE TO STERILIZE FLUID HAVING POOR UV TRANSMISSION

(76) Inventors: Sung Chul Lee, Seoul (KR); Jin Auck Kim, Seoul (KR); Yu Sup Kim, Hanam-si (KR)

(*) Notice: Subject to any disclaimer, the term of this patent is extended or adjusted under 35 U.S.C. 154(b) by 0 days.

(21) Appl. No.: 13/639,764

(22) PCT Filed: Nov. 1, 2010

(86) PCT No.: PCT/KR2010/007597
§ 371 (c)(1),
(2), (4) Date: Oct. 5, 2012

(87) PCT Pub. No.: WO2011/126192
PCT Pub. Date: Oct. 13, 2011

(65) Prior Publication Data
US 2013/0026389 A1    Jan. 31, 2013

(30) Foreign Application Priority Data
Apr. 7, 2010  (KR) .................. 10-2010-0031781

(51) Int. Cl.
*C02F 1/32* (2006.01)
*G01N 21/33* (2006.01)
*A61L 2/10* (2006.01)

(52) U.S. Cl.
USPC ............ 250/432 R; 250/504 R; 250/365; 250/436; 250/438; 250/433; 422/24; 422/186.3; 210/94; 210/107; 210/748.1

(58) Field of Classification Search
USPC .......... 250/432 R, 436, 438, 433, 504 R, 250/365; 422/24, 186.3; 210/94, 107, 748.1
See application file for complete search history.

(56) References Cited

U.S. PATENT DOCUMENTS
6,139,726 A * 10/2000 Greene ................. 210/94
6,258,265 B1 * 7/2001 Jones ................... 210/202

FOREIGN PATENT DOCUMENTS
| JP | 03-207364 | 9/1991 |
| JP | 08-066677 | 3/1996 |
| JP | 2004-050169 | 2/2004 |
| KR | 10-0505079 | 7/2005 |
| KR | 20-0396115 | 9/2005 |
| KR | 10-2010-0011882 | 2/2010 |

OTHER PUBLICATIONS

International Search Report for PCT/KR2010/007597 Mailed on Aug. 9, 2011.

* cited by examiner

*Primary Examiner* — Nikita Wells
(74) *Attorney, Agent, or Firm* — Christopher Paul Mitchell

(57) ABSTRACT

The present invention relates to a UV fluid sterilizer, which is suitably formed to sterilize fluid having poor UV transmission. According to the present invention, the UV fluid sterilizer includes a plurality of UV sterilization units. The UV sterilization units include: small quartz tubes; inside UV lamps mounted in the small quartz tubes for radiating UV rays at the inside of fluid; large quartz tubes concentrically mounted outside the small quartz tubes for forming the flow spaces of the fluid; spring type coils spirally fixed to the outer diameter surfaces of the small quartz tubes for applying rotation force to the fluid; and UV transmission shrinks films for fixing the spring type coils to the outer diameter surfaces of the small quartz tubes in close contact and preventing foreign substances from being trapped in the flow spaces of the fluid, and are characterized in that a plurality of outside UV lamps are provided outside the large quartz tubes for radiating UV rays to the fluid, which flows through the UV sterilization units, from the outside.

4 Claims, 6 Drawing Sheets

UV FLUID STERILIZER SUITABLE TO STERILIZE FLUID HAVING POOR UV TRANSMISSION

RELATED APPLICATIONS

This application is a 371 application of International Application No. PCT/KR2010/007597, filed Nov. 1, 2010, which in turn claims priority from Korean Patent Application No. 10-2010-0031781, filed Apr. 7, 2010, each of which is incorporated herein by reference in its entirety.

TECHNICAL FIELD

The present invention relates to a UV (Ultraviolet ray) fluid sterilizer, and in particular to a UV fluid sterilizer which makes it possible to effectively sterilize a fluid which has a low UV transmissivity.

BACKGROUND ART

The UV sterilization is directed to a physical sterilization method using light and is concerned on a technology killing microorganism by preventing it from growing and differentiating in such a way to destroy microorganism DNA information by means of the operations of 254 nm wavelengths in UV waves.

The UV sterilization way has been generally used for the sake of the sterilization of microorganism in fluid (or waterborne microorganism). The fluid to be sterilized must have a certain level of UV transmissivity for the reasons that the sterilization UV wavelength is very short, 254 nm, so it can be easily absorbed by turbidity or chromaticity, which results in low transmissivity.

When the transmissivity of the UV sterilization with respect to fluid reaches 60% (or 40~50% in some companies), it is judged to be economical. When the transmissivity of the fluid is below 40%, UV is not generally applied to the UV.

For these reasons, the sterilization of the fluid the transmissivity of which is low is almost dependent on heat. When the sterilization on the fluid by means of heat is performed, over energy costs a lot, and lots of side effects occur as some components in the fluid is destroyed by high heat.

The UV transmissivity represents the intensity that a UV with a wavelength of 254 nm transmits through a fluid filled in a 1 cm crystal cell, and the intensity is expressed in percentage. The transmissivity of UV is generally above 98% in case of a drinkable water from a spring, and 96% in case of a raw water from a tap, and 60~70% in case of a wasting water from a sewage.

The transmissivity of UV grows lower when there is a substance formed in a benzene structure such as pentose or hexose like an organic substance or a sugar syrup which is a component among fluids which absorbs UV like Fe, Mn, etc.

A fluid having a low transmissivity is a green vegetable juice (kale, water parsley, pomegranate, carrot, etc.), fruit juice beverage (orange, apple, pomegranate, etc.), tree juice (painted maple sap, maple tree sap, etc.), alcohol drinks (traditional wine, Korean wine, apple wine, etc.), various health beverages, sauce and seasoning (soy sauce, permission vinegar, fructose, etc.), lubricant, medicine, other high density and UV non-transmittable liquid which needs sterilization.

In particular, the green vegetable juice is a juice from the vegetable as natural organic vegetables are collected and pressed by a press; however ordinary bacteria counting to 10,000~100,000 (cfu/mL) per mL are found after pressing the vegetable. Most of the companies directly deliver to the customers within one day so as to prevent any spoilage during the distribution. The customers are guided to drink all the stuff after it is opened.

If the green vegetable juice is placed at a room temperature, lots of microorganism grows and the container becomes barrel-shaped in one day by means of the microorganism. In order to prevent the above mentioned problems, the sterilization of the microorganism is desperately needed, but the conventional art does not fully perform the sterilization by way of the UV.

DISCLOSURE OF INVENTION

Accordingly, the present invention is made to improve the problems encountered in the conventional art and it is an object of the present invention to provide a UV fluid sterilizer which makes it possible to effectively perform a UV sterilization even when a UV transmissivity is low in such a way that the thickness of a fluid flowing around a UV lamp is made in a thin film shape to make sure that a transmission sterilization and a surface sterilization by a UV can be concurrently performed, and the flow of the fluid is made turbulent, and the UV is emitted to both the inner side and outer side with respect to the fluid flowing turbulently in the shape of a thin film.

To achieve the above objects, there is provided a UV (Ultraviolet ray) fluid sterilizer, comprising a plurality of UV sterilization units; and wherein each UV sterilization unit comprising a small crystal tube; an inner UV lamp installed in the small crystal tube for emitting UV from the inner side of the fluid; a big crystal tube concentrically installed at the outer side of the small crystal tube for forming a flow space of the fluid; a spring coil fixed in a spiral shape at an outer diameter surface of the small crystal tube for providing a rotational force to the fluid; and a UV transmission contraction film which allows the spring coil to come into close contact with an outer diameter surface of the small crystal tube and serves to prevent impurities from sticking on a flow space of the fluid, and wherein a plurality of outer side UV lamps are provided at an outer side of the big crystal tube for externally emitting UV to the fluid flowing through the UV sterilization unit.

The big crystal tube and the small crystal tube can be substituted with a Teflon tube.

In addition, the inner side UV lamp and the outer side UV lamp are bar-shaped UV lamps which are installed in parallel from the crystal tube.

ADVANTAGEOUS EFFECTS

The UV fluid sterilizer according to the present invention is configured to make a fluid flow in a shape of a thin film while forming a turbulent flow, so the scanning efficiency of a UV lamp rises, and the UV is emitted to both the inner side and the outer side of the fluid flowing in a shape of a thin film and in a form of turbulent, so the scanning surface area increases two times as compared to the conventional UV fluid sterilizer which emits a UV only at the inner side of the fluid, so it is possible to effectively sterilize the fluid which has low UV transmissivity.

The flow of the fluid can be made smoother with the aid of a UV transmission contraction film installed at the outer surroundings of a spring coil, and small size impurities contained in the fluid do not gather as they are caught on the coil spring, thus enhancing sterilization efficiency.

- Descriptions of the reference numerals-

| | |
|---|---|
| 10: UV sterilization unit | 11: inner side UV lamp |
| 12: small crystal tube | 13: spring coil |
| 14: UV transmission contraction film | 15: big crystal tube |
| 20: UV sensor | 30: outer UV sensor |

BEST MODES FOR CARRYING OUT THE INVENTION

The embodiments of the present invention will be described with reference to the accompanying drawings. The following embodiments are provided only for the sake of illustrative purposes, and an ordinary person in the art can modify or change within the scopes that the technical concepts do not change. So, it should be interpreted that the scope of the present invention does not limit the following embodiments.

Figure 1:
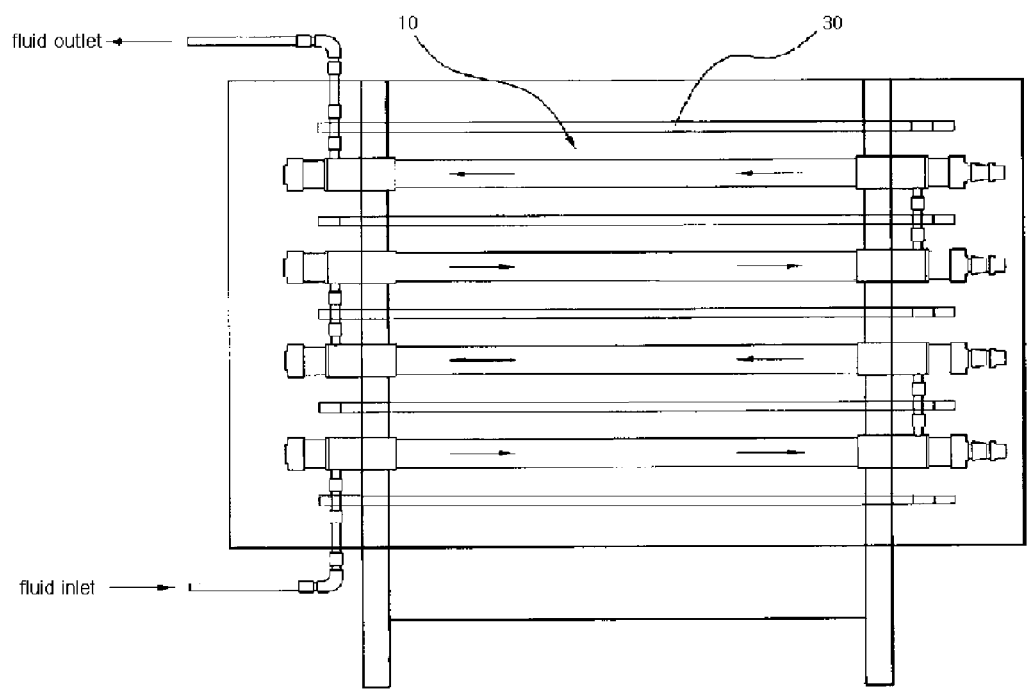
FIG. 1 is a schematic front view illustrating a UV fluid sterilizer according to an embodiment of the present invention.
Figure 2:
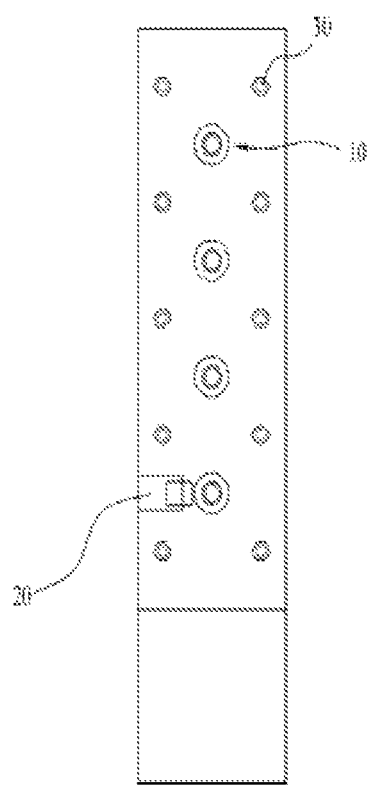
FIG. 2 is a side view of FIG. 1.
Figure 3:
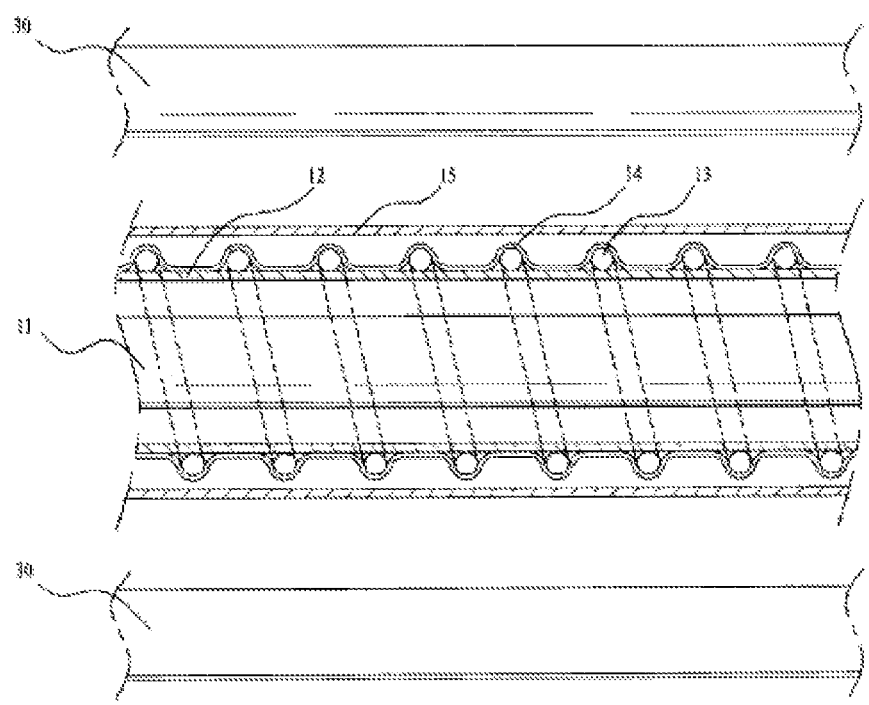
FIG. 3 is a cross sectional view shown by enlarging a UV sterilization unit of FIG. 1.
Figure 4:
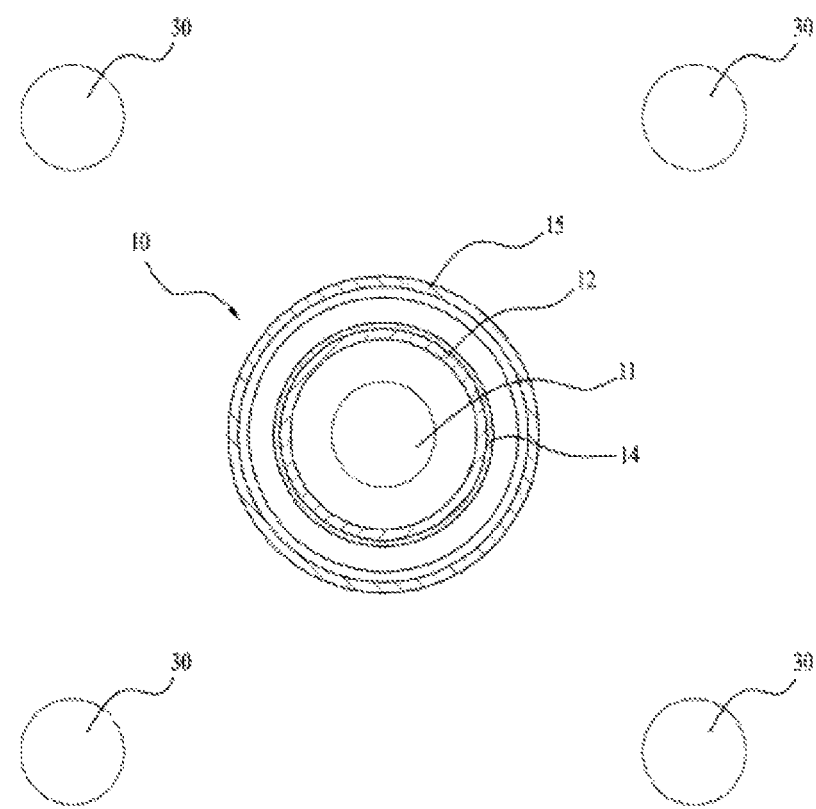
FIG. 4 is a vertical cross sectional view of FIG. 3.

FIGS. 1 and 2 are schematic front and side views of a UV fluid sterilizer according to an embodiment of the present invention, and FIG. 3 is a cross sectional view shown by enlarging a UV sterilization unit, and FIG. 4 is a vertical cross sectional view of FIG. 3.

The UV fluid sterilizer according to an embodiment of the present invention features in that a plurality of UV sterilization units 10 are connected in series or in parallel. When the UV sterilization units 10 are connected in series, it helps enhance a sterilization efficiency, and when they are connected in parallel, it helps enhance the flow rate for sterilization process.

FIGS. 1 and 2 show the construction that the UV sterilization units 10 are connected in series. When the UV sterilization units 10 are connected in series, it is preferred that 2~5 units are grouped and connected in consideration of the differential voltages of the units. In the present embodiment, the fluid inputted into the fluid inlet is sterilized by means of the UV from the UV lamp while it passes, in sequence, through the plurality of the UV sterilization units 10 which are connected in series and then is discharged via a fluid outlet.

At the outer side of the UV sterilization units 10 are installed a plurality of bar shaped outer UV lamps 30 in parallel from the UV sterilization units 10 so as to externally emit UV to the fluid which passes through each UV sterilization unit 10. In the embodiment of the attached drawings, the outer UV lamps 30 are arranged in a square shape around each UV sterilization unit 10 when viewing in the lateral direction; however the number and arrangement of the outer UV lamps 30 are not limited thereto, and they can be modified in various shapes. At one side of the UV sterilization unit 10 is installed a UV sensor 20 for the purpose of detecting a washing state of the big crystal tube 15 when the operations of the UV fluid sterilizers stop.

FIGS. 3 and 4 are views for explaining the UV sterilization units 10. The UV sterilization unit 10 comprises an inner UV lamp 11, a small crystal tube 12, a spring coil 13, a UV transmission contraction film 14 and a big crystal tube 15.

The small crystal tube 12 and the big crystal tube 15 are preferably formed of the tubes made from crystal materials to make sure that the UV sterilization wavelengths (254 nm) can well transmit; however it might be substituted with a teflon tube that a UV can well transmit. If the crystal tube 12 is substitute with the teflon, the tube might be distorted due to the pressure of the fluid, so it is preferred to use the crystal tube.

The inner side UV lamp 11 is a bar shaped UV lamp and is installed in parallel from the small crystal tube 12 at the inner center of the small crystal tube 12, and the big crystal tube 15 has a larger inner diameter than the small crystal tube 12 and is arranged concentrically at the outer side of the small crystal tube 12 while surrounding the small crystal tube 12. So, a space is formed between the small crystal tube 12 and the big crystal tube 15 for a fluid to flow along the space.

The spring coil 13 comes into close contact with the outer diameter surface of the small crystal tube 12, thus causing the fluid flowing along the UV sterilization units 10 to have turbulent.

The UV transmission contraction film 14 is covered on the spring coil 13 and serves to fix the spring coil 13. The UV transmission contraction film 14 serves to interrupt the space in which the fibers or solid substances contained in the fluid can gather in the middle of the spinning flow due to the turbulent flow of the fluid while ensuring that the resistance of the fluid can be reduced for the sake of smooth flow of the fluid, and the energy loss due to the resistance can be prevented. The UV transmission contraction film 14 is made from a material which allows the UV sterilization wavelength to pass, and it should have a good contraction performance and should withstand a UV sterilization wavelength.

The outer side UV lamp 30 is provided in multiple numbers at the outer side of the big crystal tube 15 to be in parallel from the big crystal tube 15. It is preferred that each outer side UV lamp 30 is arranged symmetrically with an equal distance from each other when viewing from the inner side UV lamps 11.

Figure 6:
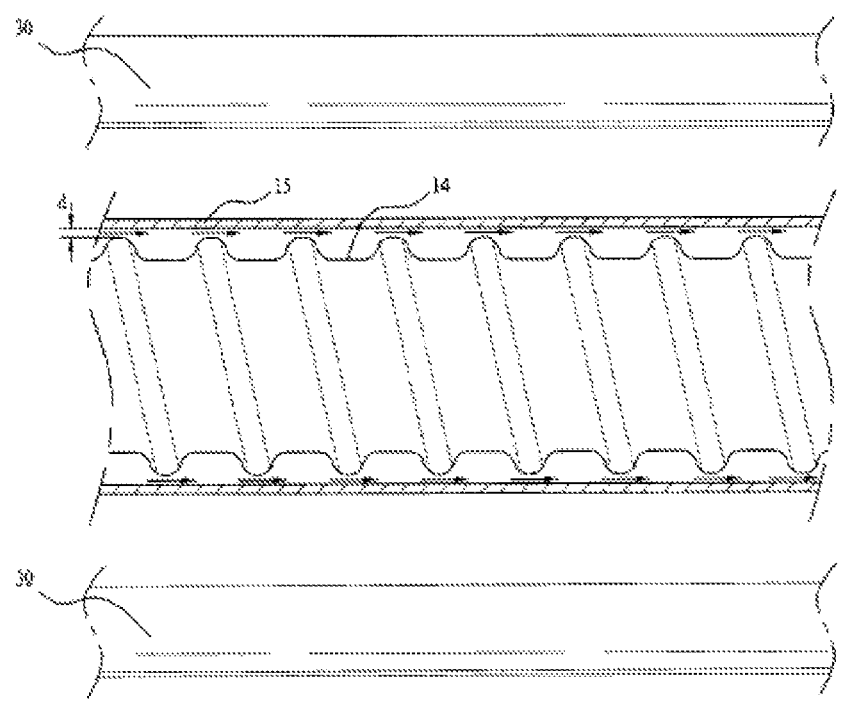
FIG. 6 is a view for explaining a state that a fluid flows in a straight shape with the aid of a gap between a big crystal tube and a spring coil.

The inner diameter of the big crystal tube 15 is larger than the outer diameter of the UV transmission contraction film 14, and a gap (d) is formed between the outer diameter of the UV transmission contraction film 14 and the inner diameter of the big crystal tube 15 for the fluid to flow along the gap as shown in FIG. 6. So, the fluid grows turbulent with the aid of the straight flow by means of the gap (d) and the spinning flow due to the spring coil 13. At this time, as the gap (d) grows narrower, an ideal turbulent flow formation condition is made; however a fiber or a solid substance might be caught on the gap (d) depending on the kinds of the fluid, so it is preferred that the gap (d) is formed to have a certain width.

In order for the fluid flowing along the concentric cross section area to uniformly receive the UV from the UV lamps, it is preferred that the fluid is made turbulent. The thusly generated turbulent flow helps prevent small solid impurities contained in the fluid from sticking on the inner diameter surface of the big crystal tube 15 and the outer diameter surface of the UV transmission contraction film 14, thus preventing the worsening of the sterilization function when the UV is interrupted by means of the solid impurities. In other words, it is preferred that the UV sterilization function cannot worsen when the sterilizer operates for a long time.

Figure 5:
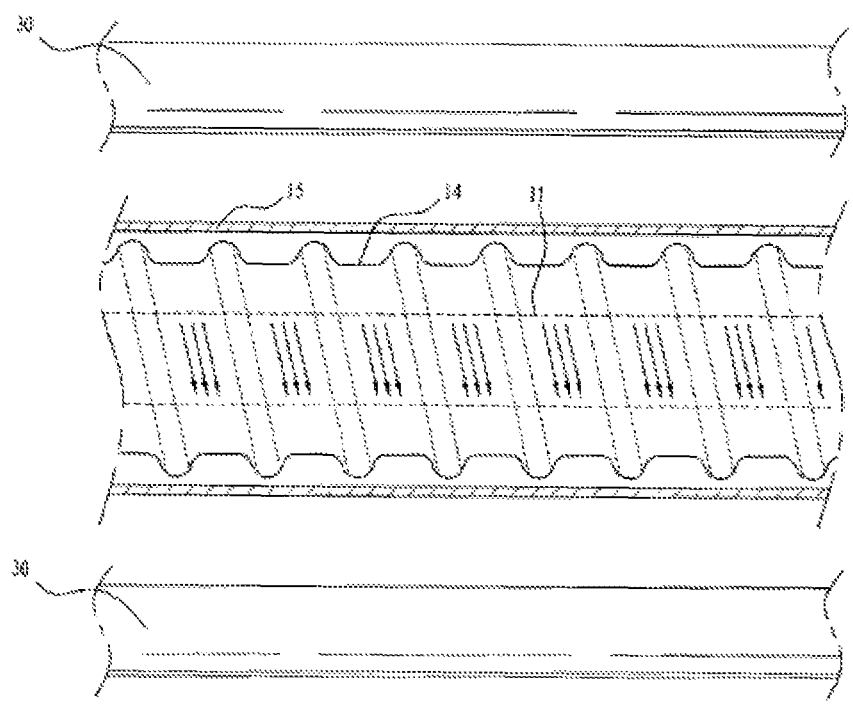
FIG. 5 is a view for explaining a state that a fluid flows in a spiral shape with the aid of a coil spring.

FIGS. 5 and 6 are views for explaining the flow of the fluid on the concentric cross section area. Here the fluid has a straight flow through a gap (d) between the big crystal tube 15 and the UV transmission contraction film 14 and a spiral flow along the configuration of the spring coil 14. When the spiral flow is made to have turbulent by adjusting the ratio between the flow rate and the concentric cross section area, the turbulent spiral flow collides with the straight flow, thus enhancing the turbulent flow of the fluid flowing through the gap (d). The turbulent factors in the spiral flow are affected by means of the flow rate and the flow passage cross section area.

The laminar flow and the turbulent flow appearing in the flow of the fluid are generally classified by means of Reynold's number. When Reynold's number is lower than 2,000, it means the laminar flow, and when it is higher than 4,000, it means the turbulent flow. The Reynold's number is determined by means of the density of the fluid, flow rate, the diameter of the tube, the viscosity, etc. Assuming that the flow rates are same, the smaller the diameter of the tube, the higher the Reynold's number, and as the viscosity grows lower and the density (temperature) grows lower, the Reynold's number rises.

So, it is possible to change the fluid flow to a turbulent flow by properly adjusting the width of the gap (d) and the pitches of the spring coil 13. If the pitch space of the spring coil 13 is too narrow, the spring coil 13 does not generate the resistance in the flow, and if it is two wide, the generation of the turbulent flow is interfered.

The UV fluid sterilizer according to an embodiment of the present invention is directed to enhancing the UV sterilization efficiency since the UV is emitted from the inner UV lamps 11 and the outer side UV lamps 30 while the fluid is flowing in a turbulent form through the gap between the big crystal tube 15 and the UV transmission contraction film 14.

Since the UV is concurrently emitted from the inner and outer sides of the fluid to the fluid, the UV sterilization efficiency can be enhanced since the UV scanning surface area increases more than two times as compared to the conventional UV fluid sterilizer.

The invention claimed is:

1. A UV (Ultraviolet ray) fluid sterilizer, comprising:
a plurality of UV sterilization units; and
wherein each UV sterilization unit comprising:
a small crystal tube;
an inner UV lamp installed in the small crystal tube for emitting UV from the inner side of the fluid;
a big crystal tube concentrically installed at the outer side of the small crystal tube for forming a flow space of the fluid;
a spring coil fixed in a spiral shape at an outer diameter surface of the small crystal tube for providing a rotational force to the fluid; and
a UV transmission contraction film which allows the spring coil to come into close contact with an outer diameter surface of the small crystal tube and serves to prevent impurities from sticking on a flow space of the fluid, and wherein a plurality of outer side UV lamps are provided at an outer side of the big crystal tube for externally emitting UV to the fluid flowing through the UV sterilization unit.

2. The sterilizer of claim 1, wherein the big crystal tube is formed of a Teflon tube.

3. The sterilizer of claim 1, wherein the small crystal tube is formed of a Teflon tube.

4. The sterilizer of claim 1, wherein the inner side UV lamp and the outer side UV lamp are bar-shaped UV lamps which are installed in parallel from the crystal tube.

* * * * *